United States Patent
Choi et al.

(10) Patent No.: US 9,000,165 B2
(45) Date of Patent: Apr. 7, 2015

(54) PROCESS FOR THE PREPARATION OF ANHYDROUS ARIPIPRAZOLE CRYSTAL FORM II

(75) Inventors: Soo Jin Choi, Yongin-si (KR); Seong Soo Oh, Yongin-si (KR); Yong Suk Jin, Ansan-si (KR); Yong Tae Kim, Daejeon (KR); Seung Jae Lee, Daejeon (KR); Jeong Hyun Son, Suwon-si (KR)

(73) Assignee: Daewoong Pharmaceutical Co., Ltd., Seongnam-si (KR)

( * ) Notice: Subject to any disclaimer, the term of this patent is extended or adjusted under 35 U.S.C. 154(b) by 0 days.

(21) Appl. No.: 14/008,167

(22) PCT Filed: Mar. 30, 2012

(86) PCT No.: PCT/KR2012/002349
§ 371 (c)(1),
(2), (4) Date: Dec. 10, 2013

(87) PCT Pub. No.: WO2012/134206
PCT Pub. Date: Oct. 4, 2012

(65) Prior Publication Data
US 2014/0114071 A1    Apr. 24, 2014

(30) Foreign Application Priority Data

Mar. 31, 2011  (KR) ................ 10-2011-0029931

(51) Int. Cl.
| | | |
|---|---|---|
| C07D 401/06 | (2006.01) | |
| C07D 215/227 | (2006.01) | |
| A61K 31/4709 | (2006.01) | |
| A61K 31/496 | (2006.01) | |

(52) U.S. Cl.
CPC ........ C07D 215/227 (2013.01); A61K 31/4709 (2013.01); A61K 31/496 (2013.01)

(58) Field of Classification Search
CPC .................................................... C07D 215/227
See application file for complete search history.

(56) References Cited

U.S. PATENT DOCUMENTS

| 5,006,528 | A  | 4/1991 | Oshiro et al. |
| 7,714,129 | B2 | 5/2010 | Eisen-Nevo et al. |
| 7,872,132 | B2 | 1/2011 | Chinnapillai et al. |

FOREIGN PATENT DOCUMENTS

| CN | 101277935 A | 10/2008 |
| JP | 02-191256 A | 7/1990 |
| KR | 10-2007-0073878 A | 7/2007 |
| KR | 10-2007-0088750 A | 8/2007 |
| WO | WO 03/026659 A1 | 4/2003 |
| WO | WO 2005/058835 A2 | 6/2005 |
| WO | WO 2005058835 A2 * | 6/2005 |
| WO | WO 2007/041414 A1 | 4/2007 |
| WO | WO 2007041414 A1 * | 4/2007 |

* cited by examiner

Primary Examiner — Noble Jarrell
Assistant Examiner — John S Kenyon
(74) Attorney, Agent, or Firm — Seed IP Law Group PLLC

(57) ABSTRACT

The present invention relates to a process for preparation of aripiprazole crystal form II by recrystallizing aripiprazole in a mixture of acetone and 1-methoxy-2-propanol or a single solvent of 1-methoxy-2-propanol. The simple process according to the present invention can produce aripiprazole crystal form II with high purity and high yield in a mass scale.

7 Claims, 3 Drawing Sheets

PROCESS FOR THE PREPARATION OF ANHYDROUS ARIPIPRAZOLE CRYSTAL FORM II

TECHNICAL FIELD

The present invention relates to a novel process for the preparation of anhydrous aripiprazole crystal form II.

BACKGROUND ART

Aripiprazole having the structure shown in the following Formula 1 is, an atypical anti-psychotic and antidepressant drug, and exhibits a potent affinity for dopamine D2 and D3, serotonin 5-HT1A and 5-HT2A receptors; a mild affinity for dopamine D4, serotonin 5-HT2C and 5-HT7, α1-adrenaline agonist and histamine H1 receptors; and a mild affinity for serotonin reuptake sites.

[Formula 1]

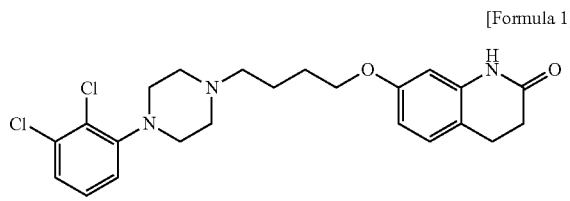

Aripiprazole has no detectable affinity for cholinergic muscarinic receptors. Similarly to other drugs having an efficacy against schizophrenia, the mechanism of action of aripiprazole has not been identified. However, it has been proposed that the efficacy of aripiprazole is mediated through the combination of an activity for partial acceleration at the D2 and 5-HT1A receptors (agonist) and an activity for antagonism at the 5-HT2A receptors (antagonist).

U.S. Pat. No. 5,006,528 and Japanese Early Published Patent No. 02-191256 disclose that the crystal of anhydrous aripiprazole can be prepared either by recrystallizing anhydrous aripiprazole from ethanol or by heating aripiprazole hydrate at a temperature of 80° C.

Further, in a bulletin of the Fourth Japan-Korea Symposium for Separation Techniques (Oct. 6-8, 1996), it was disclosed that anhydrous aripiprazole can be present in the crystal forms I and II.

Aripiprazole crystal form I can be prepared by recrystallizing aripiprazole from ethanol solution or by heating aripiprazole hydrate at a temperature of 80° C. However, anhydrous aripiprazole crystal form I obtained from such a method is disadvantageous in view of the fact that it has a significant hygroscopic property. Thus, upon exposure to moisture the anhydrous crystal form I can absorb the moisture and be converted into the hydrate form, and is thus inferior to the anhydrous crystal form II in view of bioavailability and resolvability.

Aripiprazole crystal form II can be prepared by heating the hydrate of aripiprazole crystal form I at a temperature of 130 to 140° C. for 15 hours (see the bulletin of the Fourth Japan-Korea Symposium). However, this method cannot be readily applied to industrial scale production of anhydrous aripiprazole, due to the disadvantages involved in long working time at a high temperature.

WO 07/041414 discloses that aripiprazole crystal form II can be prepared by seeding aripiprazole crystal form II into acetone solvent containing the starting aripiprazole such as compound 1, compound 2, crystal form I, crystal form II, crystal form VI, crystal form VIII, crystal form X, crystal form XXI, etc., and then slurrifying the mixture at 30° C. to 50° C. for 2 to 22 hours. However, this method is also not suitable for industrialization due to the problems involved in slurrification under a warming condition for a long period of time.

DISCLOSURE OF INVENTION

Technical Problem

Thus, the present inventors have conducted extensive study to develop an industrially useful process capable of efficiently producing aripiprazole crystal form II, and consequently, have succeeded in developing the process of the present invention. The process according to the present invention can improve the purity of aripiprazole crystal form II, lower the manufacturing cost through shortening the processing time, and provide a consistent and reproducible results.

Solution to Problem

According to the present invention, a single solvent of 1-methoxy 2-propanol or a mixture of acetone and 1-methoxy-2-propanol is selected to prepare anhydrous aripiprazole crystal form II. The desired anhydrous aripiprazole crystal form II can be obtained with a high purity by adding aripiprazole crystal to the selected solvent, heating the mixture to dissolve the crystal therein, seeding aripiprazole crystal form II and then isolating aripiprazole crystal form II from the solution.

Advantageous Effects of Invention

According to the present invention, which provides a novel process for preparing anhydrous aripiprazole crystal form II, the following advantages can be provided:

Firstly, aripiprazole crystal is recrystallized providing the effect of improving the purity of aripiprazole;

Secondly, as compared to the prior art, a significantly small quantity of the solvent can be used, resulting in lowering of the manufacturing costs;

Thirdly, as compared to the prior art the processing time can be reduced, resulting in the lowering of manufacturing costs;

Fourthly, it can be readily applied to scaled mass production.

BEST MODE FOR CARRYING OUT THE INVENTION

The process of the present invention is characterized in that aripiprazole crystal form II can be obtained by recrystallizing aripiprazole in the mixed solvent of acetone and 1-methoxy-2-propanole or the single solvent of 1-methoxy-2-propanol.

Figure 1:
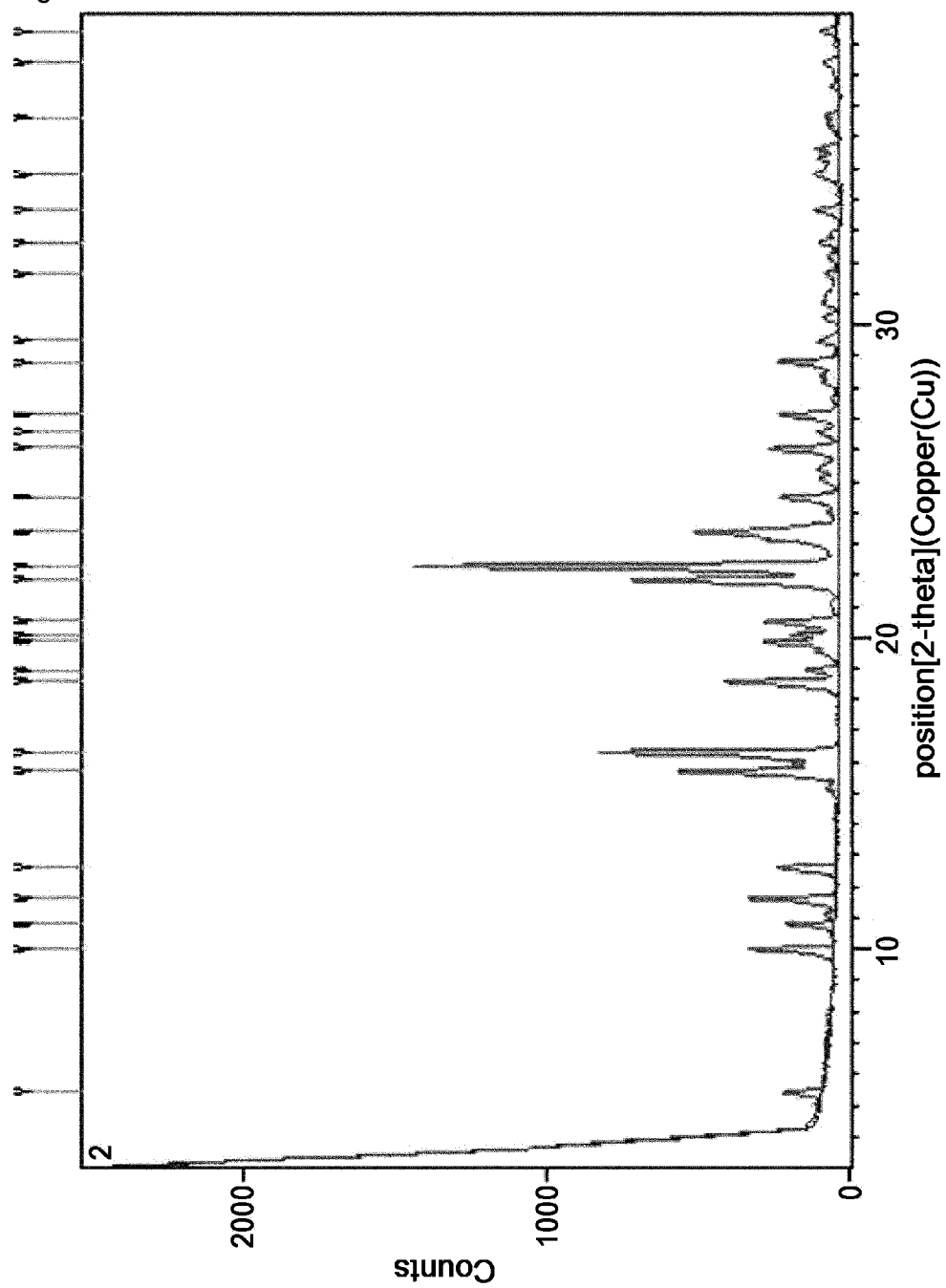
FIG. 1 shows the X-ray powder diffraction (XRD) pattern of aripiprazole crystal form II as obtained according to the method disclosed in the prior art (WO 05/058835).

The aripiprazole crystal form II obtained according to the present invention, publicly known in WO 05/058835, is characterized in that it shows X-ray powder diffraction peaks at 2θ=16.5, 18.7, 21.9, 22.4 and 23.5°±0.2°. The aripiprazole crystal form II used as the seeding crystal in the process according to the present invention can be prepared, either previously or just before its use, according to the method disclosed in WO 05/058835. The result of XRD of aripiprazole crystal form II as obtained according to the method of WO 05/058835 is shown in FIG. 1.

Specifically, the present invention relates to the process for preparation of anhydrous aripiprazole crystal form II, which comprises the following steps:

a) introducing aripiprazole crystal into a mixed solvent of acetone and 1-methoxy-2-propanol or a single solvent of 1-methoxy-2-propanol;

b) dissolving the crystals with heating and stirring;

c) seeding the crystal of aripiprazole crystal form II; and d) isolating the desired aripiprazole crystal form II from the solution.

In general, the quantity of aripiprazole crystal form II used as the seeding crystal is about 0.01 to 1% by weight on the basis of the starting aripiprazole.

As the starting aripiprazole any aripiprazole such as crystal form I, crystal form III, etc. can be used, but aripiprazole crystal form III is preferably used. The aripiprazole crystal form III has been disclosed in the bulletin of the Fourth Japan-Korean Symposium (Oct. 6-8, 1996).

Preferably, the solvent used is the mixture of acetone and 1-methoxy-2-propanol. In this case, a mixing ratio of the solvents is in the range of 1:1 to 25:1 (v/v), and particularly preferably, 1:1 to 5:1 (v/v) as the ratio of milliliters of acetone to milliliters of 1-methoxy-2-propanol.

The solvent is used in a quantity sufficient to completely dissolve aripiprazole. Preferably, the starting aripiprazole and the mixed solvent are used in the ratio of about 1:8 to 1:56 (w/v), more preferably about 1:8 to about 1:22 (w/v), and most preferably about 1:8 to about 1:12, as the ratio of grams of the starting aripiprazole to milliliters of the mixed solvent. For example, in the case where aripiprazole is used in the amount of 50 grams, 400 mL to 1100 mL of the mixed solvent can be used. In the case where dissolution is affected with using the mixed solvent, the reaction mixture is heated at a temperature of 45° C. to 60° C., preferably refluxed with stirring, to completely dissolve the aripiprazole. Further, 1-methoxy-2-propanol single solvent is used in the ratio of about 1:5 to about 1:30 (w/v), more preferably about 1:5 to about 1:10 (w/v) as the ratio of grams of aripiprazole to milliliters of the solvent. In the case where the single solvent is used for dissolution, the reaction mixture is heated at a temperature of 70° C. to 90° C.

After dissolving aripiprazole in the mixed solvent of acetone and 1-methoxy-2-propanol, the aripiprazole crystal form II is seeded preferably at a temperature of 35° C. to 65° C. In the case where 1-methoxy-2-propanol single solvent is used, the temperature for the seeding step is preferably in the range of 35° C. to 75° C.

Upon completion of the seeding, the slurry is cooled down to a temperature of 0° C. to 30° C., preferably 0° C. to 10° C. The slurry can then be filtered to isolate the anhydrous aripiprazole crystal form II.

The method for said isolation step can further include the step of washing and drying the anhydrous aripiprazole crystal form II. Washing is preferably carried out using acetone, 1-methoxy-2-propanol, etc. Preferably, the anhydrous aripiprazole crystal form II is dried at a temperature of about 40° C. to about 80° C., more preferably at a temperature of 50° C. to 70° C., under reduced pressure.

The process according to the present invention exhibits the advantage of shortening the processing time as compared to the prior methods. Specifically, the bulletin of the Fourth Japan-Korean Symposium (Oct. 6-8, 1996) discloses the processing time of 15 hours and WO 07/041414 discloses the processing time of 2-22 hours whereas the present invention requires a total of 10-30 minutes since the reaction mixture is cooled down immediately after seeding. Due to such a significant shortening of the processing time, the present invention shows the advantage of lowering manufacturing costs as well.

MODE FOR THE INVENTION

Hereinafter, the present invention will be more specifically illustrated by the following examples. However, the following examples are provided only to illustrate the present invention, but are not intended to limit the scope thereof.

Example 1

Figure 2:
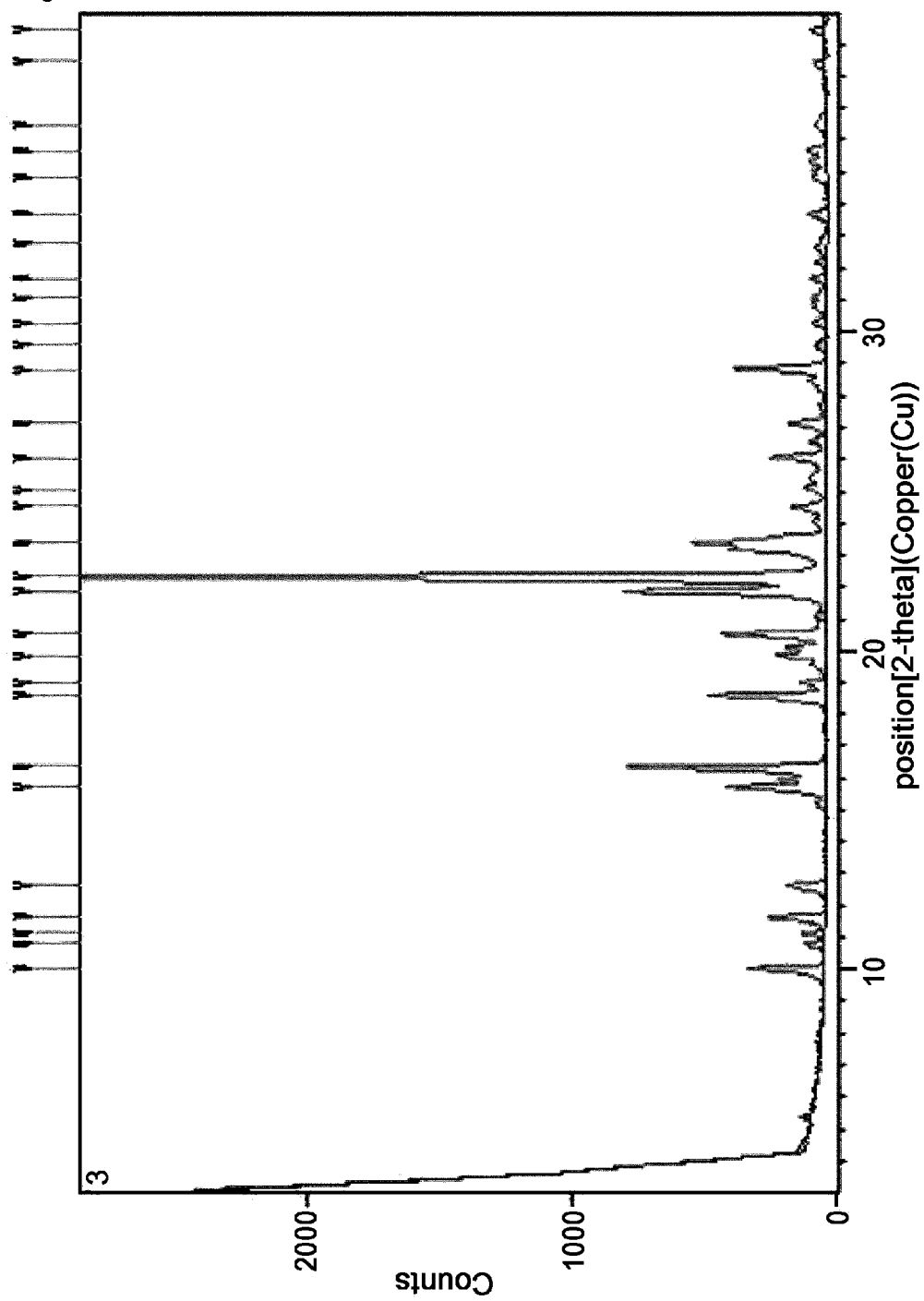
FIG. 2 shows the X-ray powder diffraction pattern of aripiprazole crystal form II as obtained according to experiment No. 1 in Example 1 of the present invention.

Preparation of Aripiprazole Crystal Form II in 1-methoxy-2-propanol Single Solvent Aripiprazole crystal form III (5 g) and 1-methoxy-2-propanol (25 mL-150 mL) were introduced into a reaction vessel having capacity of 250 mL volume. The mixture was completely dissolved by heating at 70° C. to 90° C. with stirring. 0.05 g of aripiprazole crystal form II was seeded thereto, and the mixture was cooled down to 0° C. to 10° C. and then stirred. After stirring for 30 minutes, wet aripiprazole crystal form II thus precipitated was filtered, collected and washed with 10 mL of 1-methoxy-2-propanol. The resulting crude aripiprazole crystal form II was dried under vacuum at 50° C. to 70° C. for 8 hours to obtain the dried crystal form II (yield 80%). The results of experiments thereon are summarized in the following Table 1. The X-ray powder diffraction pattern of the aripiprazole crystal form II as obtained from experiment 1 is shown in FIG. 2.

TABLE 1

| Experiment No. | Solvent | Used Quantity of Solvent | Seeding Temp. (° C.) | Cooling Temp. (° C.) | Polymorphs |
|---|---|---|---|---|---|
| 1 | 1-methoxy-2-propanol | 5 times | 70 | 5 | Form II |
| 2 |  | 10 times | 45 | 5 | Form II |
| 3 |  | 20 times | 35 | 5 | Form II |
| 4 |  | 30 times | 35 | 5 | Form II |

Example 2

Figure 3:
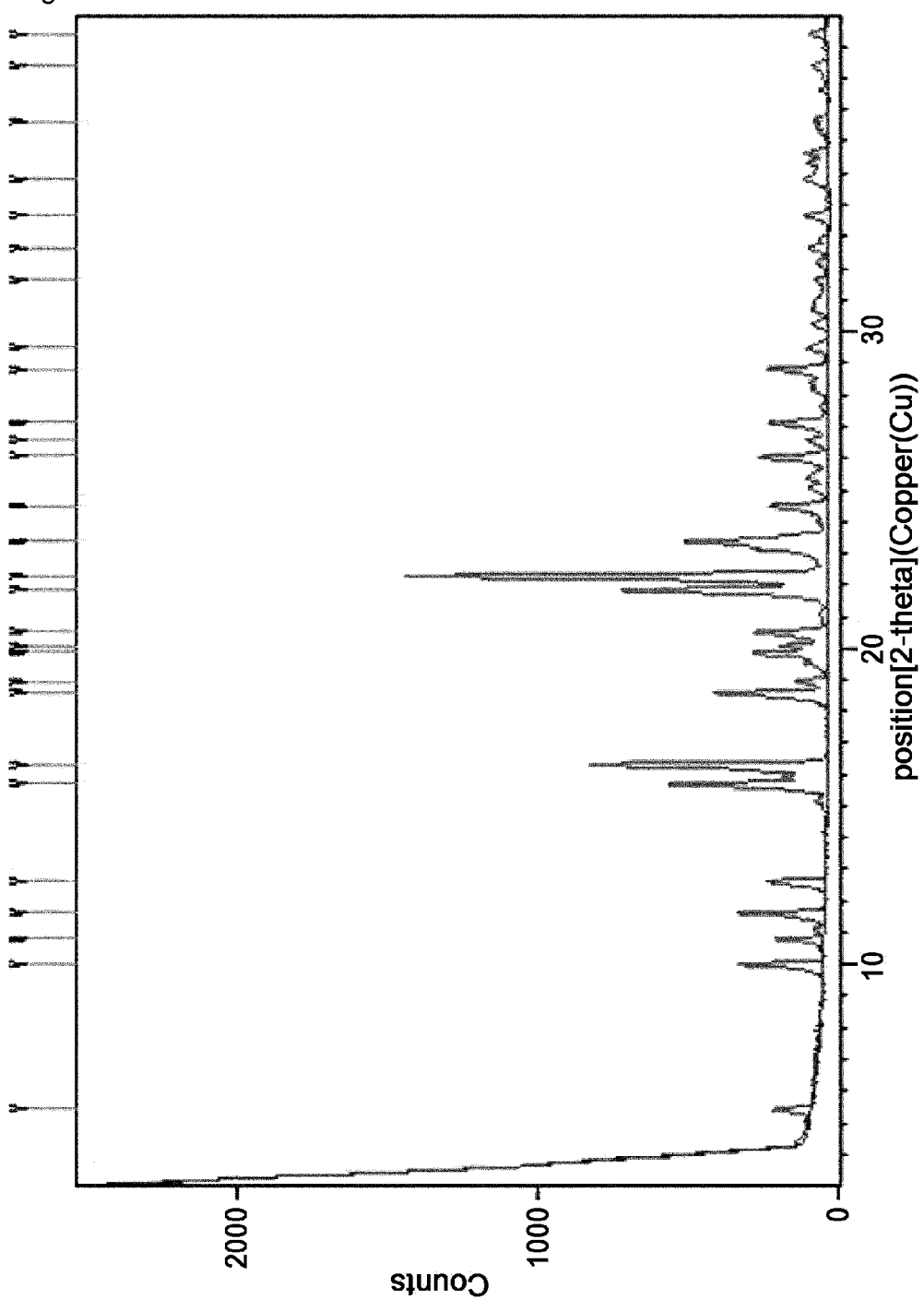
FIG. 3 shows the X-ray powder diffraction pattern of aripiprazole crystal form II as obtained according to experiment No. 1 in Example 2 of the present invention.

Preparation of Aripiprazole Crystal Form II in the Mixed Solvent of 1-methoxy-2-propanol and Acetone The starting aripiprazole in the crystal form III (4 g), acetone (24 ml-200 ml) and 1-methoxy-2-propanol (8 ml-24 ml) were introduced into a reaction vessel. The mixture was completely dissolved by heating at 45° C. to 60° C. 0.04 g of aripiprazole crystal form II was seeded thereto, and the mixture was cooled down to 0° C. to 10° C. and then stirred. Wet aripiprazole crystal form II thus precipitated was filtered, collected and washed with acetone. The resulting crude aripiprazole crystal form II was dried under vacuum at 50° C. to 70° C. for 8 hours to obtain the dried crystal form II (yield 87%). The results of experiments thereon are summarized in the following Table 2. The X-ray powder diffraction pattern of the aripiprazole crystal form II as obtained from the experiment 1 is shown in FIG. 3.

Among the results reported in the following Table 2, the experiment Nos. 5 and 6 are included as the comparative examples for comparing the effects depending on the presence or absence of the seeding step, and the crystal form B is as mentioned in WO 03/026659.

TABLE 2

| Exper. No. | Aripiprazole | Acetone | 1-methoxy-2-propanol | Seeding Temp. (° C.) | Cooling Temp. (° C.) | Polymorph |
|---|---|---|---|---|---|---|
| 1 | 4 g | 24 mL | 8 mL | 55 | 5 | Form II |
| 2 | 4 g | 80 mL | 8 mL | 45 | 5 | Form II |
| 3 | 4 g | 200 mL | 8 mL | 35 | 5 | Form II |
| 4 | 4 g | 24 mL | 24 mL | 45 | 5 | Form II |
| 5 | 4 g | 90 mL | — | No seeding | 5 | Form B |
| 6 | 4 g | 24 mL | 8 mL | No seeding | 5 | Form B |

The invention claimed is:

1. A process for preparation of anhydrous aripiprazole crystal form II, which comprises the following steps:
    a) introducing aripiprazole crystal form III into a mixed solvent of acetone and 1-methoxy-2-propanol or a single solvent of 1-methoxy-2-propanol;
    b) dissolving aripiprazole crystal form III with heating and stirring;
    c) seeding a crystal of aripiprazole crystal form II; and
    d) isolating the desired aripiprazole crystal form II from the solution.

2. The process according to claim 1, wherein the resulting anhydrous aripiprazole crystal form II shows the diffraction angles of 2θ=16.5, 18.7, 21.9, 22.4 and 23.5±0.2 in X-ray powder diffraction analysis.

3. The process according to claim 1, wherein aripiprazole crystal form III is dissolved in the mixed solvent of acetone and 1-methoxy-2-propanol with heating at 45° C. to 60° C.

4. The process according to claim 1 or 3, wherein after dissolving aripiprazole crystal form III in the mixed solvent of acetone and 1-methoxy-2-propanol, aripiprazole crystal form II is seeded thereto at 35° C. to 65° C.

5. The process according to claim 1, wherein aripiprazole crystal form III is dissolved in the single solvent of 1-methoxy-2-propanol with heating at 70° C. to 90° C.

6. The process according to claim 1 or 2, wherein after dissolving aripiprazole crystal form III in the single solvent of 1-methoxy-2-propanol, aripiprazole crystal form II is seeded thereto at 35° C. to 75° C.

7. The process according to claim 1, which further comprises the steps of:
    washing the isolated aripiprazole crystal form II using acetone or 1-methoxy-2-propanol; and
    drying the aripiprazole crystal form II at a temperature of about 40° C. to about 80° C. under reduced pressure.

* * * * *